United States Patent
Parins et al.

[19]

[11] Patent Number: 5,908,420
[45] Date of Patent: Jun. 1, 1999

[54] SURGICAL SCISSORS WITH BIPOLAR DISTAL ELECTRODES

[75] Inventors: David J. Parins, Corcoran, Minn.; Lee L. Swanstrom, Portland, Oreg.

[73] Assignee: Everest Medical Corporation, Minneapolis, Minn.

[21] Appl. No.: 08/943,543

[22] Filed: Oct. 3, 1997

[51] Int. Cl.⁶ .................................................. A61B 17/39
[52] U.S. Cl. ............................... 606/51; 606/46; 606/52; 606/170; 606/174
[58] Field of Search ................................. 606/45, 46, 48, 606/49, 50, 51, 52, 174, 170

[56] References Cited

U.S. PATENT DOCUMENTS

5,342,381  8/1994  Tidemand .
5,352,222  10/1994  Rydell .
5,540,685  7/1996  Parins et al. .

*Primary Examiner*—Lee Cohen
*Attorney, Agent, or Firm*—Nikolai, Mersereau & Dietz, P.A.

[57] ABSTRACT

A surgical scissors instrument having disposed at its distal end two bipolar electrode structures which function to coagulate tissue immediately prior to its being severed by scissor action. The instrument comprises a first scissors blade having a distal end and a second scissors blade having a distal end, wherein at least one of the blades is pivotable in relation to the other blade. A first electrically insulated bipolar electrode structure is disposed longitudinally distally from the distal end of the first scissors blade, and a second electrically insulated bipolar electrode structure is disposed longitudinally distally from the distal end of the second scissors blade. The instrument thereby permits a physician to precisely apply electrical energy only at the distal end of the scissor's blades, and to thereafter immediately cut coagulated tissue situated immediately forward of the blade members.

13 Claims, 6 Drawing Sheets

SURGICAL SCISSORS WITH BIPOLAR DISTAL ELECTRODES

BACKGROUND OF THE INVENTION

This invention relates in general to surgical scissors, and in particular to a surgical scissors instrument having cooperating cutting blades and disposed at their distal ends are two forceps jaws comprising bipolar electrode structures which can function to coagulate tissue immediately prior to its being severed by scissor action of the cutting blades Electrocauterization is a process whereby blood vessels (commonly called "bleeders") in tissue or alone which are cut during a surgical procedure are sealed closed by applying electrical energy at the site to, essentially, fuse by heat the vessel opening. To provide electrical energy at the site of bleeding, an instrument capable of conducting electricity must be placed at that site. The conductive instrument may be comprised of one electrode (monopolar) which cooperates with a remote conductive body plate electrode, or the instrument may be comprised of two closely spaced electrodes (bipolar). Current passing from one electrode to the other produces the heat sufficient to seal blood vessels or to coagulate blood and other fluids so coagulable. A bipolar instrument is generally preferred by a physician since current travel is over a short distance and is predictable. A monopolar instrument usually requires electric current to travel a relatively long distance to the body plate electrode, with current directability and effect being unpredictable and possibly harmful to a patient.

Electrosurgical scissors and electrosurgical forceps individually are known in the art. Additionally, in U.S. Pat. No. 5,342,381, issued Aug. 30, 1994, commonly assigned and incorporated herein by reference, the applicant thereof describes a combination bipolar scissors and forceps instrument comprising two blade members which are configured to form forceps jaws at their distal ends and scissors blades proximal to the jaws. The entire blade members, both forceps and scissors portions, are electrically conductive, with the scissors blades electrically insulated from each other along their interfacing surfaces. Thus, both the forceps portion and the scissors portion function to coagulate tissue.

While the combination scissors and forceps instrument described above is highly effective in most surgical procedures, a physician may desire a concentration of electrical energy only at the distal ends or tips of a scissors instrument instead of having electrical energy present in the entire blade structures. Delivery of energy only distally permits the physician to exercise a more precise control of coagulation activity.

It is therefore a primary object of the present invention to provide a surgical scissors instrument having at its distal end bipolar electrode structures which function to coagulate tissue immediately prior to tissue severance by the blades of the scissors which are electrically passive.

Another object of the present invention is to provide a surgical scissors instrument wherein distally-disposed electrode structures extend distally from respective electrically insulated housings which also have secured thereto the cutting blades of the scissors.

Yet another object of the present invention is to provide a surgical scissors instrument wherein distally-disposed electrode structures additionally function as jaws of a forceps.

These and other objects of the present invention will become apparent throughout the description which follows.

SUMMARY OF THE INVENTION

The present invention is a surgical scissors instrument comprising a first scissors blade having a distal end and a second scissors blade having a distal end, wherein at least one of the blades is pivotable in relation to the other blade. A first bipolar electrode structure is disposed longitudinally distally from the distal end of the first scissors blade and is electrically insulated therefrom, and a second bipolar electrode structure is disposed longitudinally distally from the distal end of the second scissors blade and is electrically insulated therefrom. In a preferred embodiment, the first scissors blade is secured to an electrically-insulated first blade element from which the first electrode structure extends distally. In like manner, the second scissors blade is secured to an electrically insulated second blade element from which the second electrode structure extends distally. At least one of the blade elements is pivotable in relation to the other to thereby provide a severing function for the scissors blades. The instrument of the present invention thereby permits a physician to precisely apply electrical energy only at the distal end of the scissors blades, and to thereafter immediately cut coagulated tissue situated immediately forward of the blade members. The bipolar electrodes preferably function as forceps jaws.

BRIEF DESCRIPTION OF THE DRAWINGS

A presently preferred embodiment is shown in the drawing FIGS. in which.

DETAILED DESCRIPTION OF A PREFERRED EMBODIMENT

Figure 1:
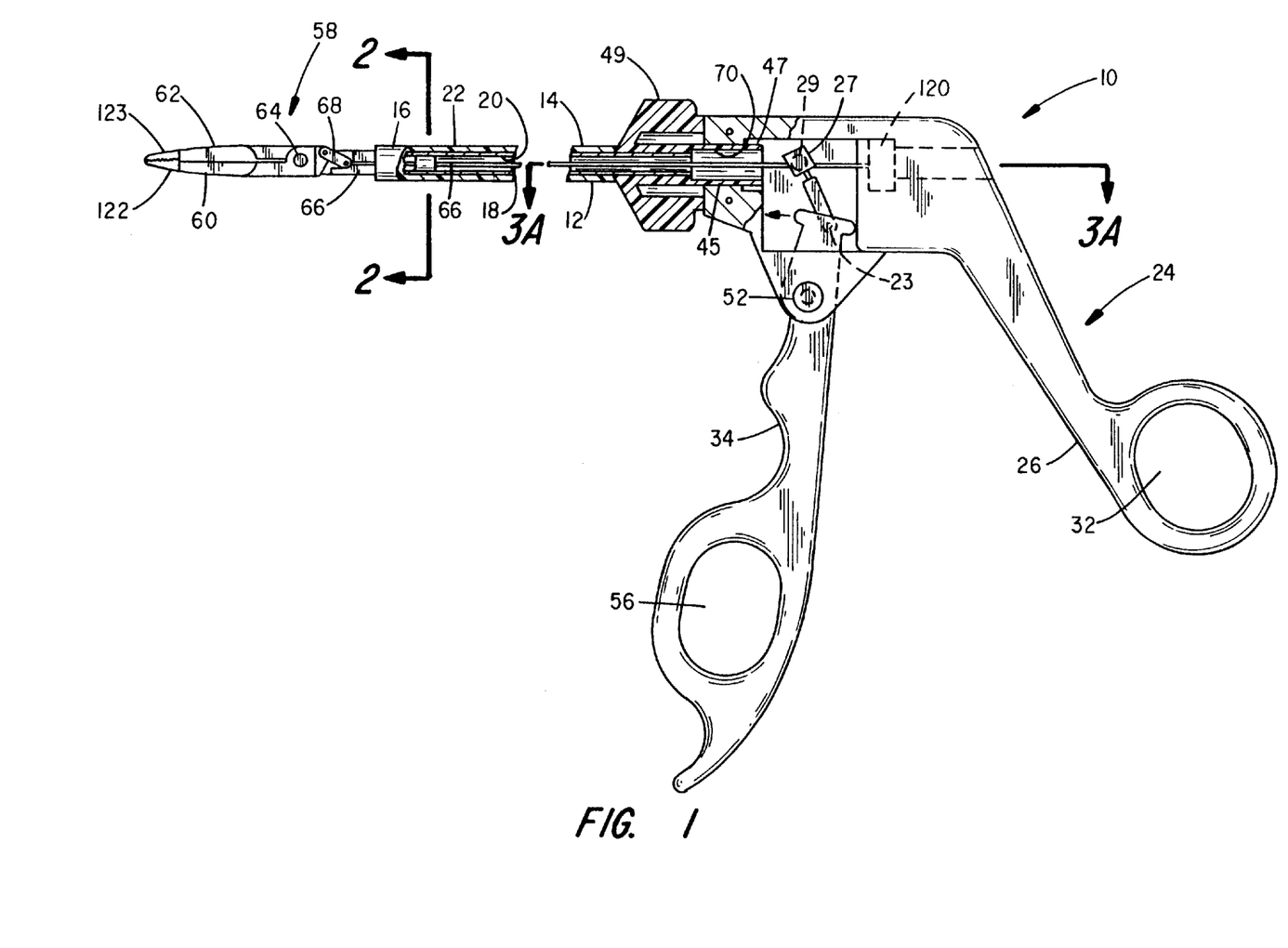
FIG. 1 is a side elevation view of a surgical scissors instrument having distal bipolar electrode structures.

Referring to FIG. 1, a scissors instrument 10 is shown for use in endoscopic or similar procedures. The instrument 10 has an elongated tubular member 12 of a diameter and length sufficient for use in cooperation with a procedure performed using a scope-type instrument. The tubular member 12 has a proximal end 14, a distal end 16 and a lumen 18 which extends for the entire length of the tubular member 12. As shown in the cross sectional view of FIG. 2, the tubular member 12 comprises a metal tube 20 coated with an electrical insulator 22. The electrical insulator 22 is preferably a polymer such as Teflon®. In addition to being an insulator, such a coating provides a lubricous surface which enhances its slidability through the lumen of an endoscope.

Disposed at the proximal end 14 of the tubular member 12 is a scissors-type handle assembly 24. The handle assembly 24 has a first handle member 26 having first and second ends, with the first end thereof having a bore 30 extending therethrough and wherein, at the distal portion thereof, the proximal end 14 of the tubular member 12 resides. The first handle member 26 does not pivot. At its second end the first handle member 26 has a loop 32 intended to receive the thumb of an operator. The handle assembly 24 additionally has a second handle member 34 which is pivotal with respect to the first handle member 26 by being pivotally mounted to the first handle member 26 with a pivot pin 52. Pivotal movement is depicted by the arrow shown in FIG. 1. A first end of the second handle member 34 has pivotally mounted thereto by pivot pin 23 an open top, U-shaped cradle member 27 in which is cradled a sphere 29 in direct communication with the distal blade members as described later. Situated at the second end of the handle member 34 is a loop 56 to receive the forefinger of the operator.

Press fit into the distal end 16 of the tubular member 12 is a pair of end effectors comprising blade and electrode assembly 58. As will be explained more fully later, the assembly 58 comprises a first blade element 60 and a second blade element 62 pivotally joined to each other by a rivet or screw 64 which extends through bores formed through the two blade elements 60, 62. Both blade elements 60, 62 are depicted as pivotally movable with respect to each other, the device can just as well be configured with only one movable blade element. The blade elements 60, 62 are preferably constructed of an electrical insulator such as a high temperature plastic or ceramic.

Figure 2:
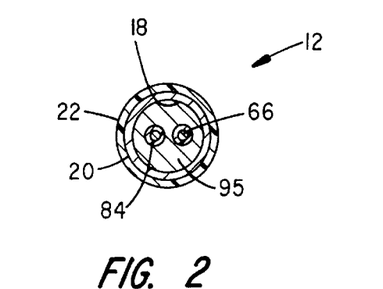
FIG. 2 is a cross section view along line 2—2 of FIG. 1.
Figure 4:
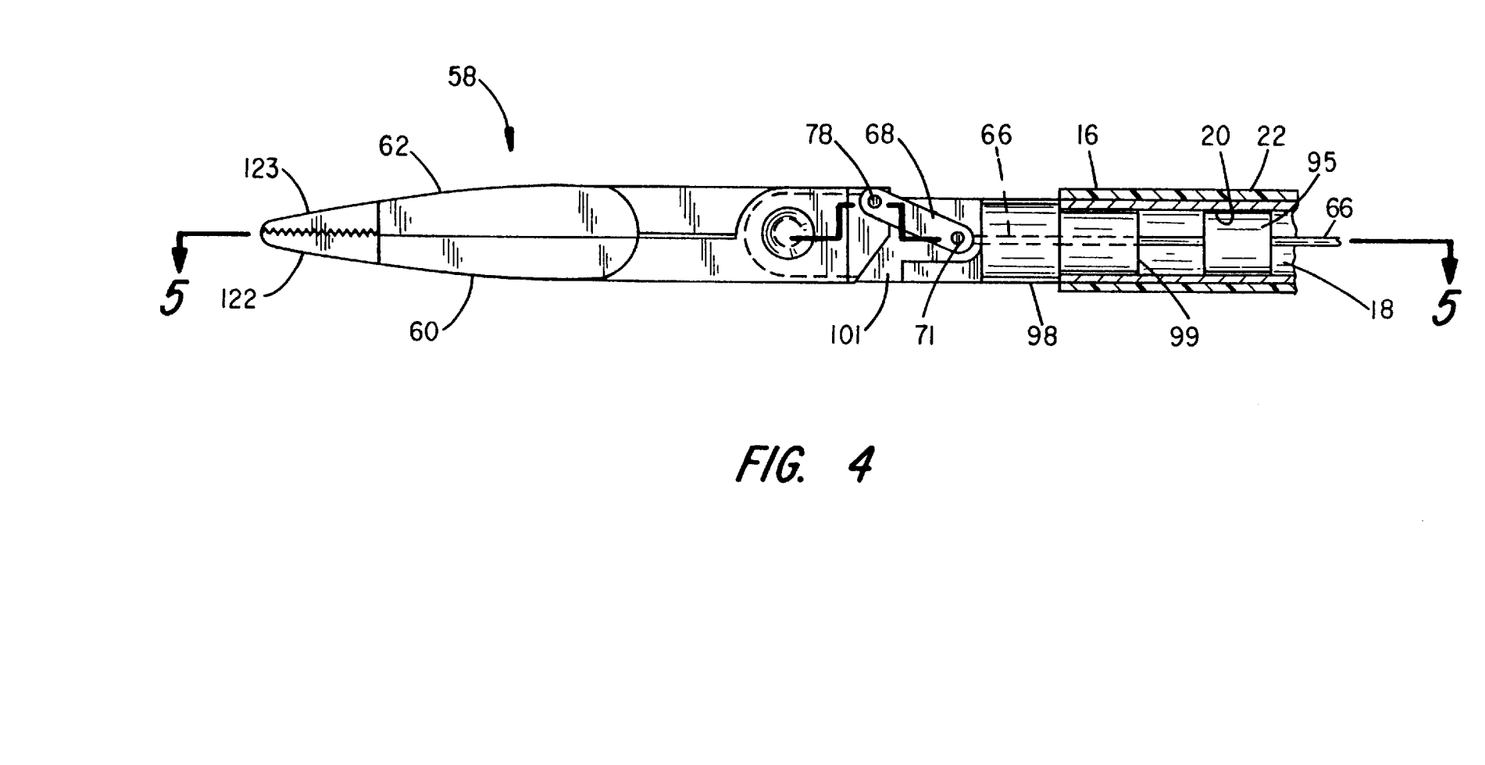
FIG. 4 is an enlarged, partially sectioned side elevation view of the distal end portion of FIG. 1.
Figure 5:
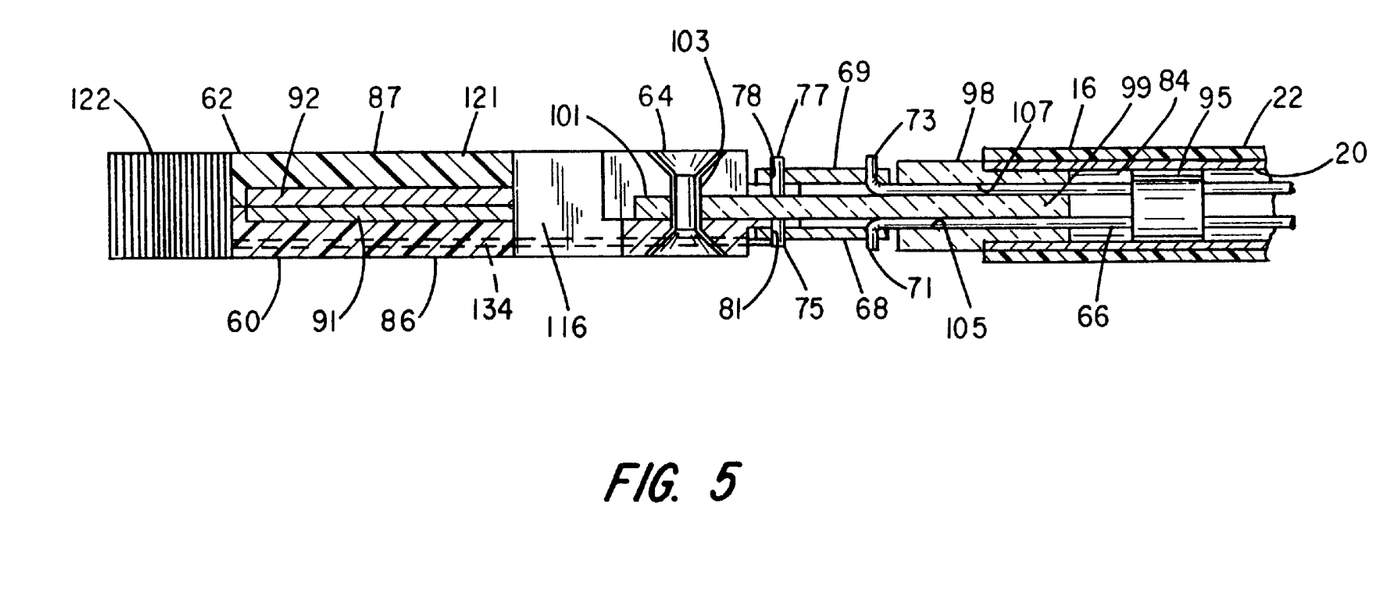
FIG. 5 is a cross section view along line 5—5 of FIG. 4.

With reference to FIGS. 1 and 2, it is seen that two rigid electrically conductive rods 66, 84, each covered with a layer of electrical insulation, extend through the lumen 18 of the tubular member 12. Referring to FIGS. 1, 4 and 5, which show the distal portion of the instrument 10, the rods 66, 84 are pivotally coupled to their respective blade elements 60, 62 by respective rigid links 68, 69. The distal ends of the rods 66, 84 are turned laterally outwardly to fit through respective proximal pivot point openings 71, 73 of the links 68, 69 to thereafter form a rivet type connection. With reference to FIG. 5, situated at each of the proximal portions of the blade elements 60, 62 in step-down sections thereof are laterally projecting posts 75, 77 which pass through distal pivot openings 78, 81 of the links 68, 69 to likewise form rivet-type connections. The rigid links 68, 69 can, therefore, pivot at each of their respective proximal and distal end portions.

Figure 3A:
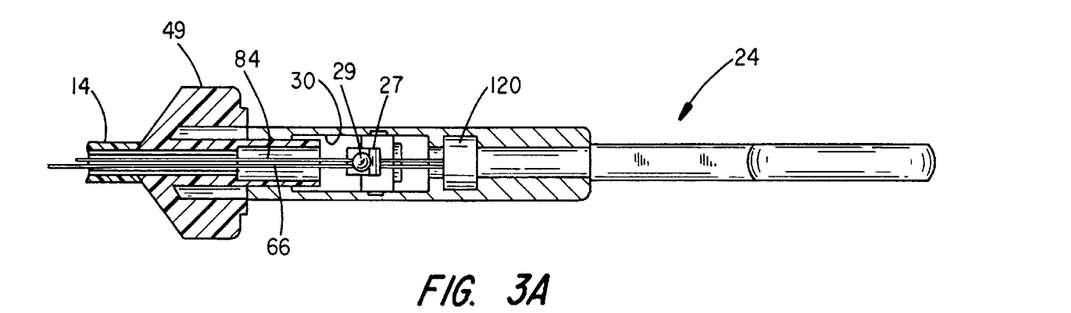
FIG. 3A is a partial cross-sectional view of the proximal portion of the instrument taken along the line 3A—3A in FIG. 1.
Figure 3B:
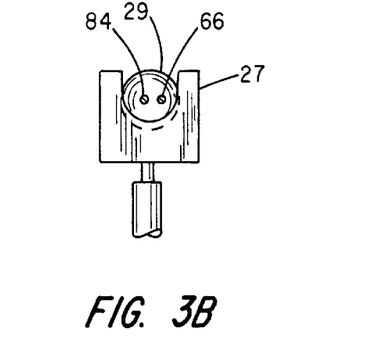
FIG. 3B is a front elevation view of a portion of a coupling which permits operability of the instrument.

As is evident in FIGS. 4 and 5, the assembly 58 includes a base 98 having a proximal portion 99 and a distal portion 101. The distal portion 101 has a bore 103 therethrough which provides a frame to which the blade elements 60, 62 are pivotally attached via a pin or screw 64. The proximal portion 99 of the base 98 is press fit within the tubular member 12 and has two parallel longitudinal bores 105, 107 through which the rods 66, 84 pass. Proximal to the base 98 within the tubular member 12 is disposed a cylindrical insulator spacer member 95 through which the rods 66, 84 pass. This insulator member 95 functions to electrically isolate the rods 66, 84 from each other while mechanically acting to maintain them in parallel, spaced relationship. The respective proximal ends of the rods 66, 84 extend proximally from the proximal end of the tubular member 12 through the sphere 29 and terminate in a free wheeling electrical connector 120 (FIG. 3A). The free wheeling connector 120 cannot move translationally in the handle assembly 24, but can freely rotate. External leads originating from an electrosurgical generator (not shown) as known in the art provide current to the connector 120 to thereby provide current to the rods 66, 84.

Because the sphere 29 is freely rotatable within the cradle member 27, the tubular member 12 and therefore the end effector assembly 58 can be rotatably moved. A knob 49 is therefor provided near the proximal end of the tubular member 12 to facilitate easy rotation by hand of the end effector assembly 58 when blade member positioning is performed by the operator. As seen in FIG. 1, the rotatable knob 49 is generally cylindrical in shape, having a bore 45 through its center along the central axis. The bore 45 is large enough to accept the tube 20 therein and allow the conductive rods 66, 84 to pass therethrough. The uninsulated proximal end of the tube 20 is frictionally inserted into the bore 45, to thereby rotate when the knob 49 is rotated. The knob 49 has an integrally formed tubular extension 70 which terminates in an annular flange 47. The handle assembly 24 has complementarily shaped internal contours which accept the extension 70 and the flange 47 to thereby allow rotation thereof within the handle assembly 24. The knob 49 is preferably constructed of nylon so that the extension 70 and annular flange 47 will have lubricous characteristics for smoother rotation inside of the handle assembly 24. Because the rods 66, 84 are mechanically connected by the insulator member 95 which is stationary within the tube 20, rotation of the knob 49 results in rotation of the tube 20 as well as the rods 66, 84 to thereby also rotate the end effector assembly 58. Concurrently, the sphere 29 is rotated because the rods 66, 84 pass therethrough to their termination in the free wheeling electrical connector 120. As is evident from FIG. 1, operation of the handle assembly 24 by pivotally moving the second handle member 34 in scissors-like action moves the cradle member 27 to thereby translationally move the sphere 29 which in turn moves both of the rods 66, 84 to thereby pivotally open and close the blade elements 60, 62 relative to one another. In this manner, dual blade movement is accomplished.

Referring to FIGS. 4 to 7, each blade element 60, 62 includes an insulator material blank 86, 87, preferably a high temperature plastic or ceramic. Affixed to and projecting outwardly from the flat inner surfaces which interface each other are metal scissors blades 91, 92. Each blade element 60, 62 thereby has a proximal scissors portion 121 and distal electrode structures, here shown as conductive metal jaws 122, 123 each extending distally from the respective blade element 60, 62. Respective electrically-conductive insulated wires 132, 134 lead from the laterally projecting posts 75, 77 through respective bores or lumens 136, 138 formed longitudinally in the blade elements 60, 62 to terminate in contact with the conductive jaws 122, 123 to thereby activate the jaws when RF current is applied. The blade members 91, 92, being insulated from the jaws 122, 123 remain electrically passive. To maintain the blades 91, 92 in cutting contact, an integrally formed ramp surface 116 is provided to one side of the distal portion 101 of the base 98 to thereby effect one of the blade elements, here as shown being blade element 62. The ramp is achieved by appropriately molding or machining the base 98 so as to leave a rise of approximately 0.005 inch, with the rise being in contact with the proximal portion of the blade element 62. When the blade elements 60, 62 are affixed to each other, the blade element 62 is biased by the ramp surface 116, thereby forcing the shearing surfaces of blades 91, 92 at the scissors portions 121 against each other as the blade elements 60, 62 are operated. The required shearing action is thereby maintained.

Figure 6:
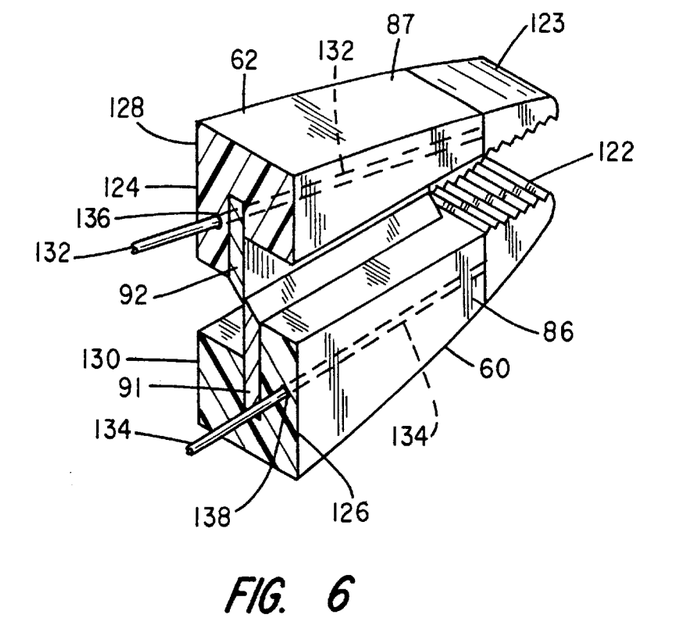
FIG. 6 is a partial perspective view of the blade members of FIG. 1.
Figure 7:
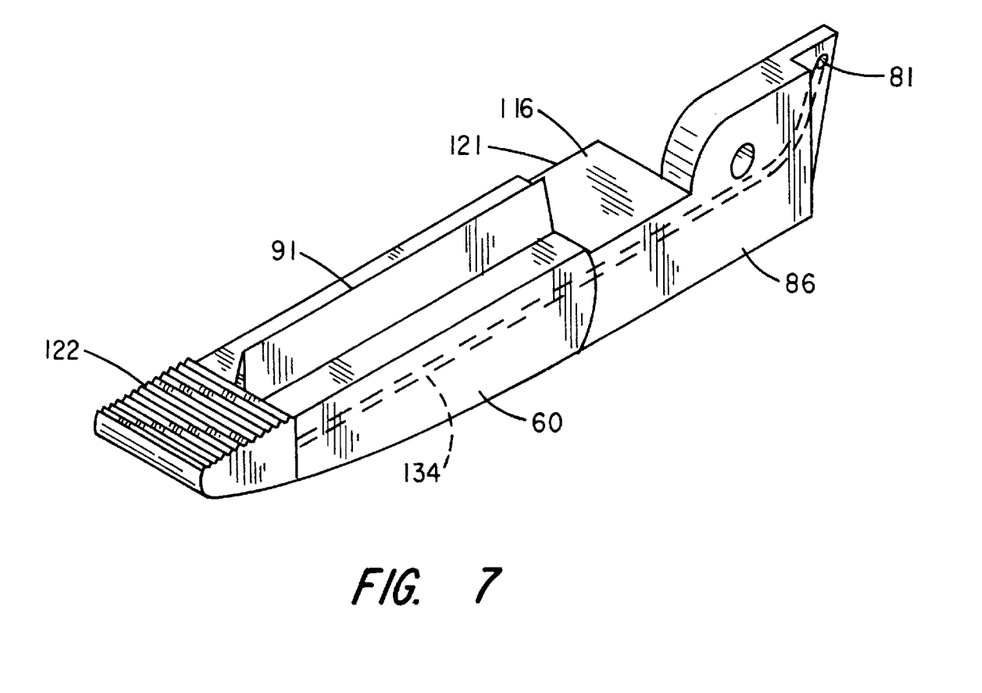
FIG. 7 is a perspective view of a single blade member of FIG. 6.

FIGS. 6 and 7 show, in perspective, the preferred blade element shape. In particular, FIG. 6 illustrates the blade elements 60, 62 in a partially open configuration. As is there apparent, the insulator-material blanks 86, 87 are uniformly tapered distally and have a constant width along their entire length. The proximal scissors portion 121 is formed by providing blanks 86, 87 with a somewhat L-shape cross-section whereby respective vertical legs 124, 126 are juxtaposed such that respective horizontal legs 128, 130 are disposed at the free ends of the vertical legs 124, 126. Blades 91, 92 are appropriately beveled at their meeting cutting edges and are bonded into slots formed in the horizontal legs, 128, 130 to thereby provide shearing action upon housing member movement. The distal ends of the blanks 86, 87 have affixed thereto the electrode-structure metal jaws 122, 123. FIG. 7 shows the single blade element 60 wherein the jaw 122 is serrated to provide a better grasping action on any tissue structures being gripped thereby. The jaw 123 secured to the other blade element 62 likewise can be complementarily serrated for improved grasping action.

While blade elements 60 and 62 are preferably formed from an insulating material, they can be metal, so long as the scissors blades 91, 92 are electrically insulated with respect to the blade elements and the blade elements are coated with insulation except for exposed forceps jaw areas defining the bipolar electrodes 122, 123.

OPERATION

In operation, the physician or other care provider directs the distal portion of the instrument 10 through the endoscope or other similar device to thereby position the end effectors 58 at the site of treatment. Thereafter, with current being supplied to the jaws 122, 123, the handle member 24 is operated to first coagulate tissue at the distal end of the instrument 10. Following that, the instrument is advanced until coagulated tissue is located between scissors blades 91, 92 whereupon actuation of the handle lever 34 causes translation of rods 66, 84 and snipping action of the blades to immediately cut the previously coagulated tissue.

Figure 8:
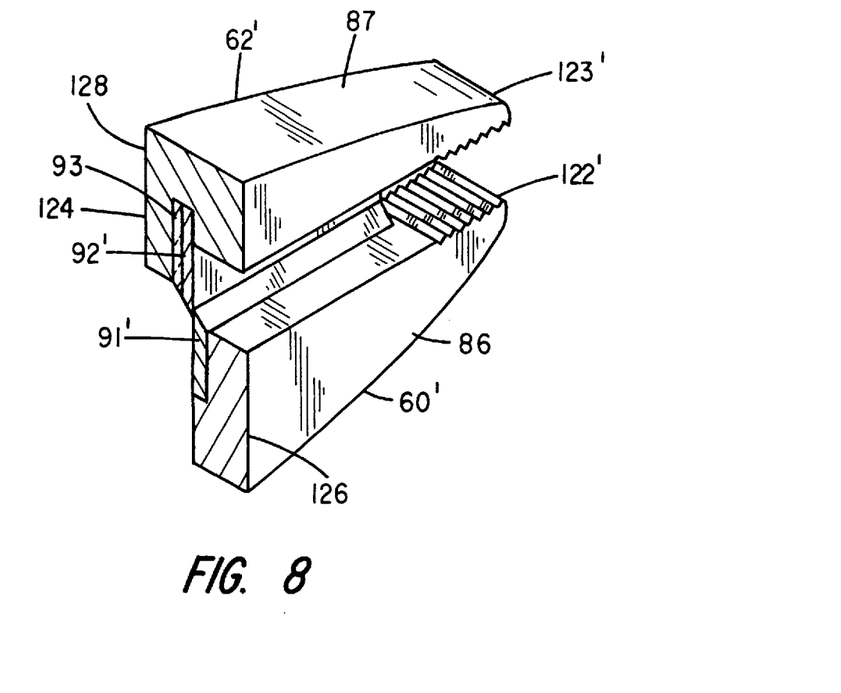
FIG. 8 is a view similar to FIG. 6 showing an alternative blade configuration.

Alternative arrangements can be devised for implementing the end effectors of the present invention. While FIG. 6 illustrates metal blade members 91 and 92 embedded in blade elements 60 and 62 formed from a suitable insulating material, such as plastic or ceramic, and with the forceps tips 122 and 123 bonded to the insulative blade elements and electrically isolated from the metal scissors blades 91 and 92, the arrangement shown in FIG. 8 can also be utilized. Here, the blade elements 60' and 62' are fabricated from metal, as are the opposed scissors blades 91' and 92'. The scissors blade 92', however, is bonded to its metal blade element 62' by means of an epoxy bonding layer 93. The epoxy layer is, of course, electrically insulating so that the metal scissors blade 92' remains out of electrical contact with the metal blade element 62'. In this arrangement, a voltage can be applied across the metal blade elements 60' and 62' contiguous with the jaws 122' and 123' without causing a short circuit when the metal scissors blades 91' and 92' contact one another. Tissue structures positioned between the jaws 122' and 123' will thus be cauterized.

Figure 9:
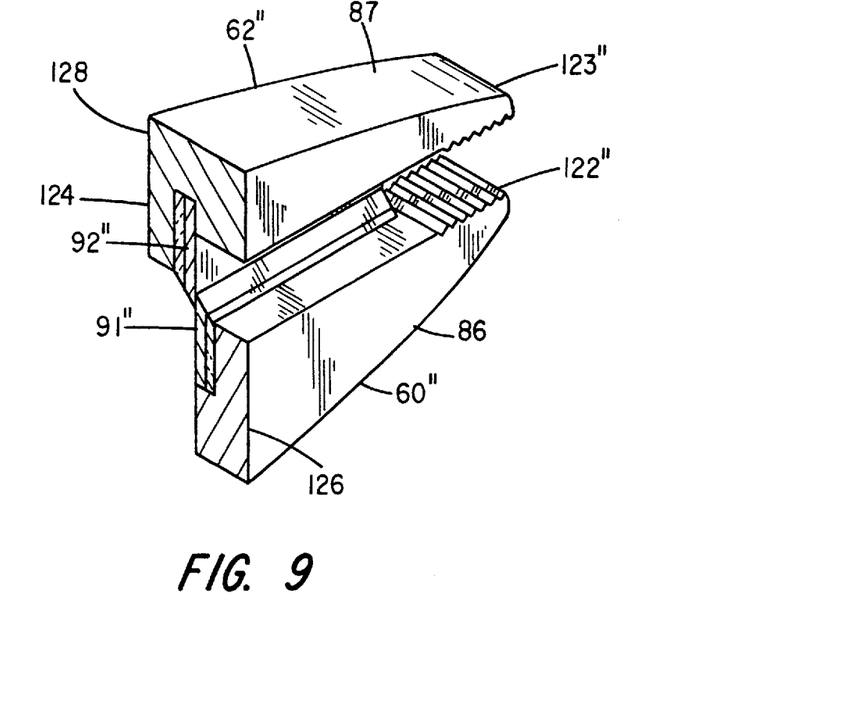
FIG. 9 is a further alternative blade member configuration.

FIG. 9 illustrates a still further embodiment of the invention wherein the blade elements 60" and 62" may again be fabricated from metal and the scissors blades 91" and 92" may also be metal. To isolate the scissors blades 91" and 92" from their respective blade elements, an epoxy or other suitable bonding agent that will act as an adhesive as well as an insulator is used to adhere the metal scissors blades to their respective metal blade elements. In this arrangement, an electrical potential can again be applied between the metal blade elements, 60" and 62" without having a short circuit condition when the scissors blades 91" and 92" engage one another during their shearing stroke. Again, any tissue disposed between the jaws 122" and 123" will be cauterized by a suitable RF voltage.

While an illustrative and presently preferred embodiment has been described in detail herein, it is to be understood that the inventive concepts may be otherwise variously embodied and employed and that the appended claims are intended to be construed to include such variation except insofar as limited by the prior art.

What is claimed is:

1. A surgical scissors instrument comprising:
   (a) first and second end effectors respectively comprising first and second electrically insulative blade elements and first and second scissors blades secured to the respective first and second insulative blade elements, the first and second scissors blades each being metal and having a distal end, at least one of the first and second end effectors configured to pivot in relation to the other of the first and second end effectors in scissors-like action;
   (b) a first bipolar electrode structure disposed longitudinally distally of the distal end of the first scissors blade on the first insulative blade element and electrically insulated from the first scissors blade, and a second bipolar electrode structure disposed longitudinally distally of the distal end of the second scissors blade on the second insulative blade element and electrically insulated from the second scissors blade; and
   (c) means for applying a voltage between the first and second bipolar electrode structures.

2. A surgical scissors instrument as claimed in claim 1 wherein each of the bipolar electrode structures is configured as a forceps jaw having a surface which interfaces with a surface of the other forceps jaw to thereby provide a first interfacing surface and a second interfacing surface.

3. A surgical scissors instrument as claimed in claim 2 wherein each of the first and second interfacing surfaces of the forceps jaw is serrated.

4. A surgical scissors instrument, comprising:
   (a) an elongated, tubular member having a proximal end, a distal end, and a lumen extending therebetween;
   (b) first and second end effectors mounted on the distal end of the tubular member for scissors-like pivotal movement of at least one of the first and second end effectors relative to the other;
   (c) the first and second end effectors each comprising an electrically insulative blade element, a metal scissors blade secured to said insulative blade element, said scissors blade having a distal end, and a bipolar electrode structure disposed longitudinally distally of the distal end of the scissors blade on said insulative blade element and being electrically insulated from said scissors blade;
   (d) means for applying a voltage between the bipolar electrode structure of the first and second end effectors; and
   (e) a handle disposed at a proximal end of the tubular member, said handle being linked with the at least one of the first and second end effectors and hand-operable to effect said scissors-like pivotal movement of said at least one of the first and second end effectors.

5. A surgical scissors instrument as claimed in claim 4 wherein each of the electrode structures is configured as a forceps jaw having a surface which interfaces with a surface of the other forceps jaw to thereby provide a first interfacing surface and a second interfacing surface.

6. A surgical scissors instrument as claimed in claim 5 wherein each of the first and second interfacing surfaces of a forceps jaw is serrated.

7. A surgical scissors as claimed in claim 4 wherein the end effectors are rotatable.

8. The surgical scissors as in claim 4 wherein the means for applying a voltage comprises a pair of conductive rods extending from the handle through the lumen of the elongated tubular member and separately conductively coupled to the bipolar electrode structure on the first and second end effectors.

9. A surgical scissors instrument comprising:

(a) first and second end effectors respectively comprising first and second electrically conductive blade elements and first and second scissors blades respectively secured to the first and second conductive blade elements, the first and second scissors blades each having a distal end, at least one of the first and second end effectors configured to pivot in relation to the other of the first and second end effectors;

(b) a first forceps jaw disposed longitudinally distally of the distal end of the first scissors blade on the first conductive blade element and electrically insulated from the first scissors blades and a second forceps jaw structure disposed longitudinally distally of the distal end of the second scissors blade on the second insulative blade element; and (c) means for applying a voltage between the first and second forceps jaws.

10. The surgical scissors instrument of claim 9 wherein the first and second scissors blades are each electrically conductive, with one of the first and second scissors blades being electrically insulated from the conductive blade element with which the one scissors blade is associated.

11. A surgical scissors instrument comprising:

(a) an elongated tubular member having a proximal end, a distal end, and a lumen extending therebetween;

(b) first and second end effectors affixed to the distal end of the elongated tubular member, said first and second end effectors respectively comprising first and second electrically conductive blade elements and first and second metal scissors blades respectively secured to the first and second conductive blade elements, the first and second scissors blades each having a distal end, at least one of the first and second end effectors configured to pivot in relation to the other of the first and second end effectors;

(c) a first forceps jaw disposed longitudinally distally of the distal end of the first scissors blade on the first blade element and electrically insulated from the first scissors blade, and a second forceps jaw disposed longitudinally distally of the distal end of the second scissors blade on the second blade element; and (d) means for applying a voltage between the first and second forceps jaws; and (e) a handle disposed at the proximal end of the tubular member, said handle being in communication with said first and second end effectors and being hand-operable to thereby produce pivotal action of the first and second end effectors relative to one another.

12. The surgical scissors instrument of claim 11 wherein each of the first and second scissors blades is electrically insulated from the first and second forceps jaws with which the first and second scissors blades are associated.

13. The surgical scissors instrument of claim 11 wherein only one of the first and second scissors blades is electrically insulated from the first and second forceps jaws with which the one scissors blade is associated.

* * * * *